United States Patent [19]

Jaunich et al.

[11] 4,259,128
[45] Mar. 31, 1981

[54] COATING CARBON ELECTRODES

[76] Inventors: Helmut Jaunich; Dieter Dunkelmann; Josef Schiffarth, all of Gelsenkirchener Str. 10, Postfach 224, D 428 Borken, Fed. Rep. of Germany

[21] Appl. No.: 825,362

[22] Filed: Aug. 17, 1977

Related U.S. Application Data

[62] Division of Ser. No. 682,873, May 3, 1976, Pat. No. 4,070,228.

[30] Foreign Application Priority Data

May 1, 1975 [GB] United Kingdom ............... 18255/75

[51] Int. Cl.³ ............................................. B29C 17/04
[52] U.S. Cl. ...................................... 156/94; 13/18 R; 156/213; 156/215; 156/475; 204/290 R; 427/113
[58] Field of Search ................. 156/94, 213, 215, 321, 156/475, 477 R, 580, 89; 13/16, 18 R; 427/113, 115; 204/290 R, 243 R

[56] References Cited

U.S. PATENT DOCUMENTS

| 3,428,545 | 2/1969 | Johnson | 427/113 X |
| 3,816,293 | 6/1974 | Veda et al. | 204/290 R |
| 3,865,662 | 2/1975 | Segal | 156/94 |
| 3,939,028 | 2/1976 | Schiffarth | 427/113 X |
| 4,132,583 | 1/1979 | Hodgson | 156/542 |

FOREIGN PATENT DOCUMENTS 722654  11/1965  Canada .................. 204/290 R Primary Examiner—David A. Simmons
Attorney, Agent, or Firm—Caesar, Rivise, Bernstein & Cohen, Ltd.

[57] ABSTRACT

A method of prolonging the useful life of a partially consumed electric arc furnace electrode which comprises holding the electrode in a fixed position, moving a plurality of electrode protection sheets substantially radially of the major axis of the electrode towards the electrode and pressing the sheets into contact with the electrode for a sufficient time to adhere the sheets to the surface of the electrode.

A frame adapted to receive at least a portion of the electrode, a plurality of carriages each reciprocable in a direction radial of the major axis of the electrode, when located in the frame, each carriage being adapted to support a protective sheet, means to urge each carriage towards the electrode, and a plurality of rollers mounted on the frame each rotatable about an axis perpendicular to the plane including the centers of the rollers and the longitudinal axis of the electrode, and each roller being biased toward the electrode.

5 Claims, 4 Drawing Figures

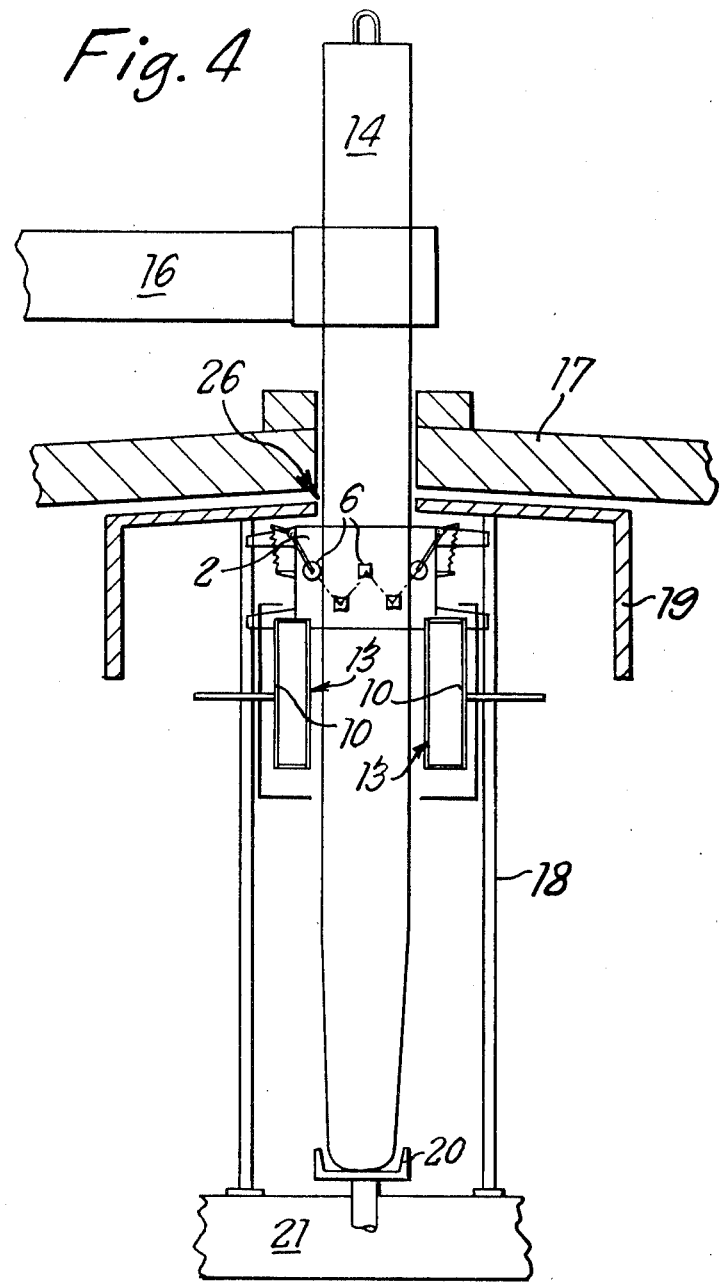

COATING CARBON ELECTRODES

This is a streamlined Divisional of Application Ser. No. 682,873, filed May 3, 1976, now U.S. Pat. No. 4,070,228.

This invention relates to the coating of carbon electrodes.

In various molten metal treatment plants use is made of massive graphite electrodes to generate heat by means of striking an arc. These electrodes are in use subject to corrosive attack, e.g. by means of oxidation. In order to reduce wastage of electrodes by this corrosion, various suggestions have been made for protecting the electrodes. These include the provision of a coating at least over that part of the electrode which in use is most liable to corrosive attack.

According to a first feature of the present invention there is provided a method of prolonging the useful life of a partially consumed electric arc furnace electrode which comprises holding the electrode in a fixed position, moving a plurality of electrode protection sheets substantially radially of the major axis of the electrode towards the electrode and pressing the sheets into contact with the electrode for a sufficient time to adhere the sheets to the surface of the electrode.

The present invention also relates to apparatus for applying protective sheets to the surface of an electric arc furnace electrode which comprises a frame adapted to receive at least a portion of the electrode, a plurality of carriages each reciprocable in a direction radial of the major axis of the electrode, when located in the frame, each carriage being adapted to support a protective sheet, means to urge each carriage towards the electrode, and a plurality of rollers mounted on the frame each rotatable about an axis perpendicular to the plane including the centres of the rollers and the longitudinal axis of the electrode, and each roller being biased toward the electrode.

The electrode protection sheets may be pre-formed tiles and preferably comprise a material which under the influence of heat causes the sheets to adhere to the electrode. Thus, an electric arc furnace electrode can be treated hot from the furnace.

The preferred electrode protection sheets may comprise a matrix having a melting point below 1000° C. and a refractory filler, preferred matrixes being graphite wetting materials, glaze-forming materials or mixtures thereof.

Examples of preferred sheets (including tiles) are disclosed in British Pat. Nos. 1,431,891 and 1,431,892.

In the apparatus of the invention, the support member may be advanced and withdrawn pneumatically, hydraulically or by other suitable means.

In some cases the adhesion obtained by advancing the protection sheet into contact with the carbon article is insufficient. Then it is preferred also to provide on the apparatus frame a plurality of rollers with axes perpendicular to the plane containing the centre of each roller and the axis of the electrode. Then the electrode to which the coating has been applied may be drawn through the rollers further to press the coating against the article.

The invention is further illustrated by way of example in the accompanying drawings wherein:

FIG. 4 shows diagramatically another form of the apparatus of the present invention in use.

Figure 1:
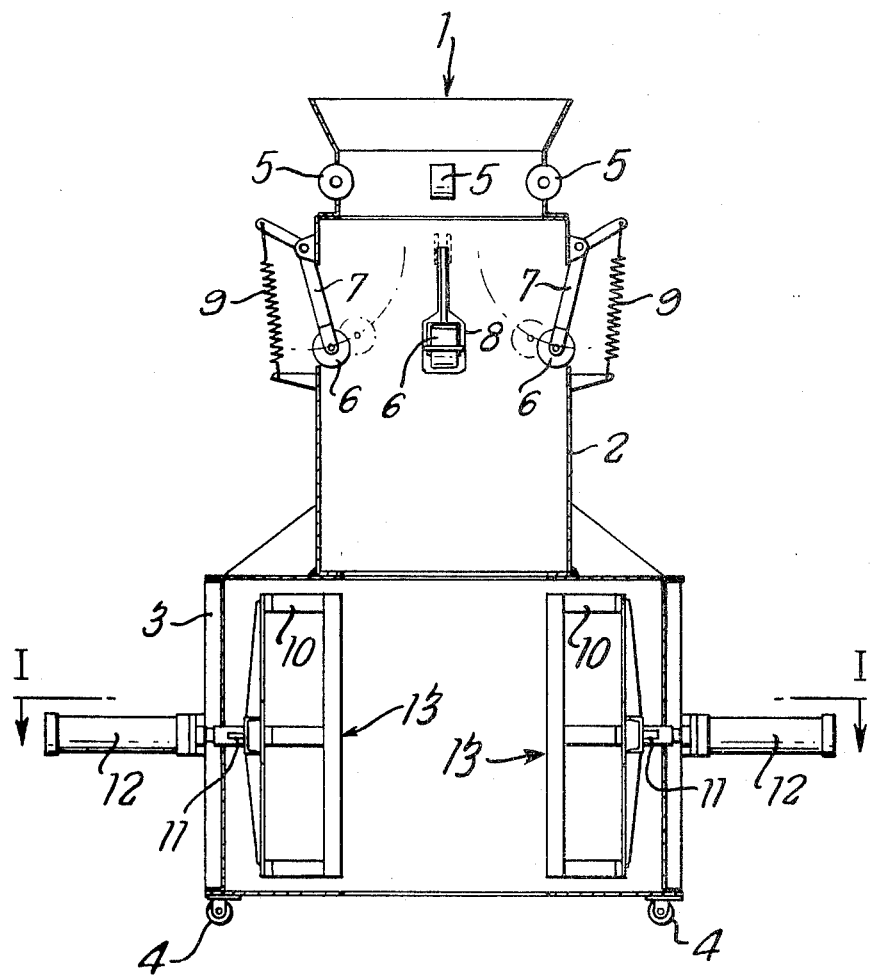
FIG. 1 shows one form of apparatus in accordance with the invention.
Figure 2:
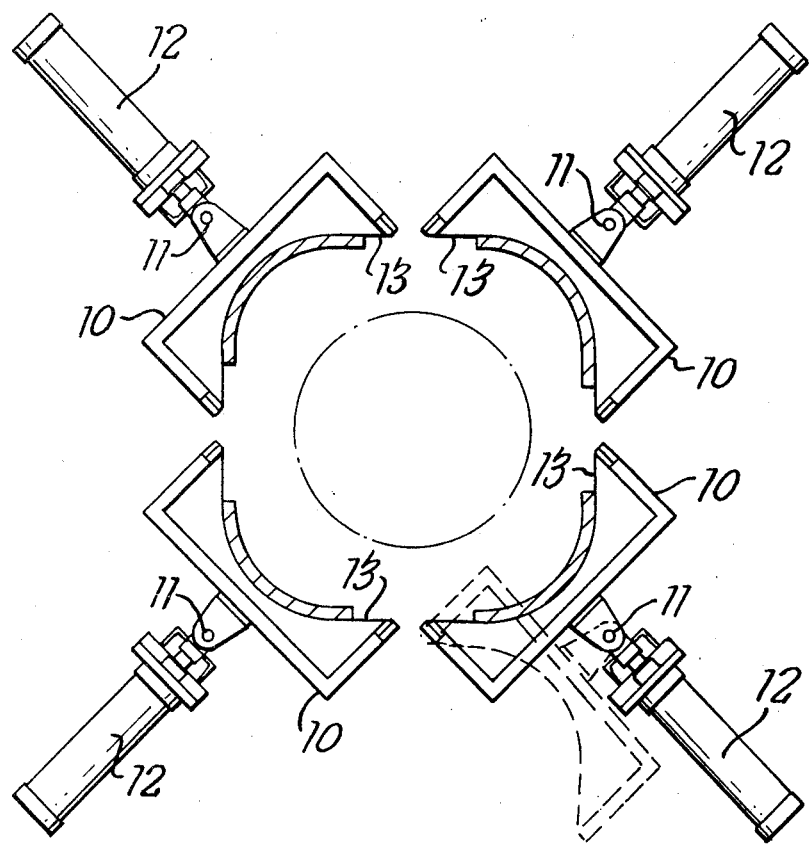
FIG. 2 is a section along I—I of FIG. 1.

With reference to FIGS. 1 and 2 the apparatus comprises an entrance 1 for an arc furnace carbon electrode to be treated. Such electrodes are generally of diameter 40–80 cm, most usually 50–60 cm. The entrance 1 leads to a hollow cylinder 2 forming part of a frame 3. The frame has castors 4 to facilitate moving the apparatus.

The entrance 1 is outwardly flared to help locate the electrode to be treated. Also rollers 5 (e.g. of graphite and usually at least four in number) are arranged around the entrance mouth to aid this location and also centering of the electrode.

A plurality of graphite rollers 6 is mounted on the outer wall of cylinder 2, by means of forks 7, with the axes of the rollers perpendicular to the plane containing their centres and the axis of the electrode. Each roller extends into the cylinder 2 through an aperture 8 in the cylinder wall. Each fork 7 is attached to a tension spring 9 also mounted on the outside of cylinder 2 such that the rollers 6 on the forks are urged inwards to the cylinder (toward the position shown as dotted circles in FIG. 1), preferably at a tension which produces in use a force of about 12 kg on an electrode from each roller.

For ease of illustrating only three graphite rollers 6 are shown in the drawings. However, it is to be appreciated that the apparatus comprises further graphite rollers, similarly mounted so that substantially the whole periphery of the electrode is contacted. In order to ensure this the rollers are arranged around the cylinder 2 in staggered fashion such that there is overlap of contact at the roller edges. It has been found that twenty four such graphite rollers are suitable for obtaining good overall contact.

Frame 3 also carries four carriages 10, each mounted via an articulated joint 11 on the piston of a pneumatic cylinder 12. The pneumatic cylinders are connected, via piping (not shown), such that only one opposing piston pair is operable at a time. Slung across each carriage 10 is a flexible stainless steel gauze 13 adapted to support a protection sheet to be applied to the electrode. If desired, each carriage can be supported on more than one pneumatic cylinder this being preferred if long sheets are to be applied to the electrode. Also, each gauze 13 may bear means for engaging and holding a protection sheet such as one or more hooks or clips.

Figure 3:
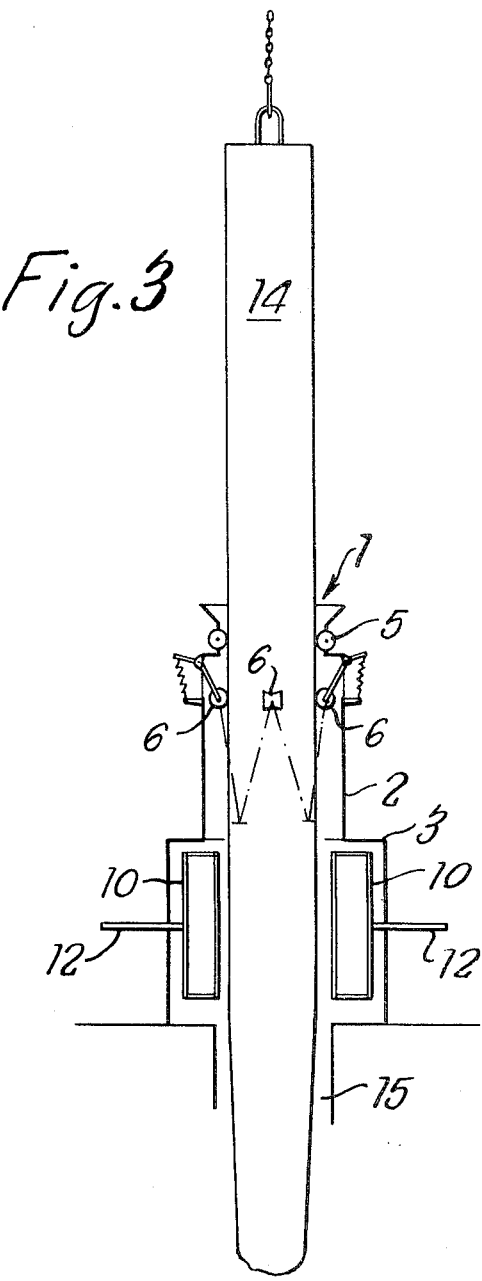
FIG. 3 shows diagramatically the apparatus of FIGS. 1 and 2 in use.

In the arrangement of FIG. 3, an electric arc furnace electrode 14 is suspended over the apparatus and received successively in the flared entrance 1, with locating and centering rollers 5, and in cylinder 2, with the graphite rollers 6 biased into engagement with the electrode. The apparatus is located on a staging or over a frame, each having an aperture 15, to receive the tip of the electrode.

In use of the apparatus, the carriages 10 are swung on joints 11 out from the frame 3 so that the gauzes 13 are exposed (to the position shown dashed in FIG. 2). A preformed tile is then mounted on each gauze 13 and the carriages are swung back into the frame.

Referring to FIG. 2, this shows in dashed line the position of the electrode and the support member ready for mounting the protective sheet and in shading the position of the protective sheets in use.

As can be seen from the shaded portions of the Figure, the tiles are curved to correspond to the outward periphery of a portion of the electrode to be coated, each tile being sized to approximately at least one quarter of the circumference of the electrode, e.g. of size 800 mm×420 mm×10 mm. Each tile is preferably multi-layered; a first layer to ensure adhesion to the electrode, a second refractory layer and a third layer which prevents adhesion to the treatment apparatus. The second and third such layers can be combined.

The hot electrode 14, preferably still hot from the furnace, is lowered (e.g. by a crane) down through the apparatus stationed above an aperture 15. The electrode is positioned such that that part to be coated is between carriages 10. The tiles on one opposing carriage pair are then driven, by pneumatic cylinders 12, against the electrode whose heat causes the tile pair to adhere. The cylinders may be e.g. of 10 cm diameter and operated at a pressure of 3 to 10 kg/cm$^2$ to give an application pressure e.g. of 20 kg/dm$^2$. The flexible nature of the gauze supports 13 for the tiles and rotation of the carriages 10 about their joint pieces 11 ensure good contact of the tiles with the electrodes even when the electrode is non-uniform.

After a suitable length of time, which will depend on how hot the electrode is e.g. 60 seconds for an 800° C. electrode, the first carriage pair is then withdrawn by their cylinders 12 and the other pair are driven forward thus applying coating to the remainder of the electrode surface. If desired there may be some overlap of the tiles to ensure complete cover, e.g. 4 mm overlap. Overlap will increase towards the lower end of the electrode owing to the taper it acquires in use.

The electrode is then drawn upwards through the apparatus. Thus the applied coating is drawn through graphite rollers 6 in cylinder 2. These rollers are urged inward and thus further press the coating on to the electrode ensuring that the coating is well adhered. As the rollers 6 are spring urged they may be used to press down the coating on electrodes of varying diameter. The concave nature of the roller surfaces, which are complementary to the shape of the facing surface of the electrode, ensures that the pressure exerted on the coating by the rollers is substantially uniform. After adherence and pressing down, the coating on the exterior of the electrode is naturally less thick than the original thickness of the sheets, e.g. a 10 mm sheet may give a final coating thickness of about 4 mm.

It should be noted that the use of graphite rollers 6 is only generally necessary at electrode temperatures below 700° C. At electrode temperatures above 700° C. the heat of the electrode itself is generally sufficient to ensure good adhesion without requiring the subsequent rolling step which, however, is beneficial.

The above use has been described with reference to the application of only one set of tiles. However, it is of course, usually necessary to coat a much larger area of electrode, i.e. to apply a plurality of tile sets. This is most conveniently done by lowering the electrode through the machine until the highest part of the electrode to be coated is between carriages 10. This highest part of the electrode is also generally the coolest and thus it is most convenient that it should be coated first. The tiles are then applied from carriages 10 as before and the electrode is raised such that the next part to be coated (which will in the meantime have cooled slightly) is between carriages 10. This of course means that the coated section passes under rollers 6 to ensure good adhesion of the coating.

Carriages 10 are swung out, reloaded and swung back again and the new tiles applied to the electrode which then is raised again ready for the next application. This is continued until the whole desired area is coated. Again, if desired to ensure complete covering, there may be an overlap of each application of tiles.

FIG. 4 shows an embodiment suitable for use in coating of an electrode e.g. during the charging of its furnace, to ensure minimum loss of manufacturing time.

To charge an electrode arc furnace the electrode on its clamp and the furnace roof are generally swung from the furnace together leaving it open for charging. In FIG. 4 like parts to FIGS. 1 to 3 are given like reference numerals.

In FIG. 4 there are shown the electrode 14 together with its clamp 16 and the furnace roof 17.

The coating apparatus comprises a main frame 18 having an insulating covering 19 apertured at 20 for receiving the electrode to be coated. Mounted in frame 18 are a cylinder 2 having a set of graphite rollers 6 spring urged inwardly as before. Below cylinder 2 are four pneumatically drivable carriages 10, also as before, each carriage having slung across it a stainless steel gauze 13 for supporting a tile to be applied. At the base of the apparatus is a pneumatic cylinder 20. The whole apparatus is on a swivelling or rotating installation 21 so that it can be brought to the necessary position for use.

In use the electrode 14, clamp 16 and furnace roof 17 are swung out, e.g. by a crane from the furnace and the electrode is lowered through aperture 26 into the apparatus. The insulating covering 19 protects the apparatus from the inevitable intense heat of the furnace roof 17.

The electrode 14 is lowered onto the cylinder 20 which can take its weight thus freeing the crane for other use.

The coating is then applied as before. Thus the tiles are loaded into carriages 10 which are then driven against the electrode where, due to the electrode heat, they adhere. The electrode is then raised (by cylinder 20) so that the applied coating is further pressed onto the electrode by rollers 6 and another coating layer may be applied.

If desired, the cylinder 2 and its associated rollers 6 may be mounted below the carriages 10. In such a construction coating would then begin at the lowest point on the electrodes. This lowest point would be coated from carriages 10 and the electrode lowered for application of the next coating above the first. The lowered coated section will then be further pressed on to the electrode for good adhesion by the rollers 6 which in this instance are below the carriages.

It should also be noted that often electrodes removed for charging in this way are usually at a temperature well in excess of 700° C. Thus cylinder 2 and its associated graphite rollers 6 may be omitted.

We claim as our invention:

1. A method of prolonging the useful life of a partially consumed electric arc furnace electrode which comprises holding the electrode in a fixed position, carrying a first pair of preformed electrode protection sheets in diametrically opposed directions radially towards the major axis of the electrode and into contact with diametrically opposed surfaces of the electrode, pressing the sheets into contact with the electrode to adhere the sheets to the surface of the electrode and thereafter rolling the sheets down by rolling pressure applying means across the sheets in a direction parallel to the major axis of the electrode.

2. The method of claim 1 additionally comprising the step of carrying a second pair of preformed electrode protection sheets in diametrically opposed directions radially towards the major axis of the electrode and at right angles to the direction said first sheets are carried through so that said second sheets are brought into contact with diametrically opposed surfaces of the electrode between said first sheets.

3. A method according to claim 1 wherein the partially consumed electrode is at elevated temperature and the electrode protection sheets comprise a material which under the influence of heat causes the sheets to adhere to the electrode surface.

4. A method according to claim 1 wherein the sheets are pressed onto the electrode surface at a pressure of at least 10 kg/dm².

5. A method according to claim 4 wherein the sheets are pressed onto the electrode surface for 30 to 300 seconds.

* * * * *